US012723092B2

(12) United States Patent
Chen et al.

(10) Patent No.: US 12,723,092 B2
(45) Date of Patent: Sep. 1, 2026

(54) ANTI-CXCR2 ANTIBODIES AND USES THEREOF

(71) Applicant: KAOHSIUNG MEDICAL UNIVERSITY, Kaohsiung City (TW)

(72) Inventors: Li-Tzong Chen, Kaohsiung City (TW); Wen-Chun Hung, Miaoli County (TW); Ko-Jiunn Liu, Miaoli County (TW)

(73) Assignee: KAOHSIUNG MEDICAL UNIVERSITY, Kaohsiung City (TW)

( * ) Notice: Subject to any disclaimer, the term of this patent is extended or adjusted under 35 U.S.C. 154(b) by 526 days.

(21) Appl. No.: 18/549,165

(22) PCT Filed: Apr. 25, 2022

(86) PCT No.: PCT/CN2022/088964

§ 371 (c)(1),
(2) Date: Sep. 5, 2023

(87) PCT Pub. No.: WO2022/228380

PCT Pub. Date: Nov. 3, 2022

(65) Prior Publication Data

US 2024/0166756 A1 May 23, 2024

Related U.S. Application Data

(60) Provisional application No. 63/179,554, filed on Apr. 26, 2021.

(51) Int. Cl.
*A61P 35/02* (2006.01)
*C07K 16/28* (2006.01)
*A61K 39/00* (2006.01)

(52) U.S. Cl.
CPC .......... *C07K 16/2866* (2013.01); *A61P 35/02* (2018.01); *A61K 2039/505* (2013.01); *A61K 2039/545* (2013.01); *C07K 2317/24* (2013.01); *C07K 2317/565* (2013.01); *C07K 2317/76* (2013.01)

(58) Field of Classification Search
CPC ............ C07K 16/2866; C07K 2317/24; C07K 2317/565; C07K 2317/76; A61P 35/02; A61K 2039/505; A61K 2039/545
USPC ........................................................ 424/133.1
See application file for complete search history.

(56) References Cited

FOREIGN PATENT DOCUMENTS

WO WO-2014170317 A1 * 10/2014 ......... C07K 16/2866

* cited by examiner

*Primary Examiner* — Yan Xiao
(74) *Attorney, Agent, or Firm* — Hannah Tien

(57) ABSTRACT

Anti-CXCR2 antibodies that recognize CXCR2 and inhibit the activity of CXCR2, and the use of the anti-CXCR2 antibodies in the treatment of pancreatic cancer and leukemia.

10 Claims, 6 Drawing Sheets

Specification includes a Sequence Listing.

| | no | hIgG | anti-CXCR2 mAb 40ug | anti-CXCR2 mAb 80ug |
|---|---|---|---|---|
| HMC-1 | 0.4 | 6.6 | 64.1 | 98.8 |
| MiaPaCa II | 0.4 | 9.3 | 83.7 | 88.3 |
| Panc-1 | 0.3 | 8.2 | 83.5 | 92.8 |

rhIL-8-Gi cAMP-MiaPaCa II cell

HTRF ratio 2500.0
2000.0
1500.0
1000.0
500.0
0.0

Control
rhIL-8
hIgG
hIgG+rhIL-8
Anti-CXCR2 mAb
Anti-CXCR2 mAb+rhIL-8

SEQUENCE LISTING

```
<160> NUMBER OF SEQ ID NOS: 11

<210> SEQ ID NO 1
<211> LENGTH: 237
<212> TYPE: PRT
<213> ORGANISM: Artificial Sequence
<220> FEATURE:
<223> OTHER INFORMATION: Light chain of the humanized anti-CXCR2
      monoclonal antibody

<400> SEQUENCE: 1
```

```
Met Lys Leu Pro Val Arg Leu Leu Val Leu Met Phe Trp Ile Pro Val
1               5                   10                  15

Ser Ser Ser Asp Ile Val Met Thr Gln Thr Pro Leu Ser Leu Ser Val
            20                  25                  30

Thr Pro Gly Gln Pro Ala Ser Ile Ser Cys Arg Ser Ser Leu Ser Leu
        35                  40                  45

Val His Ser Asn Gly Asp Thr Tyr Leu His Trp Tyr Leu Gln Lys Pro
    50                  55                  60

Gly Gln Ser Pro Gln Leu Leu Ile Tyr Lys Val Ser Asn Arg Phe Ser
65                  70                  75                  80

Gly Val Pro Asp Arg Phe Ser Gly Ser Gly Ser Gly Thr Asp Phe Thr
                85                  90                  95

Leu Lys Ile Ser Arg Val Glu Ala Glu Asp Val Gly Val Tyr Tyr Cys
            100                 105                 110

Ser Gln Ser Thr His Val Pro Thr Phe Gly Gln Gly Thr Lys Leu Glu
        115                 120                 125

Ile Lys Arg Thr Val Ala Ala Pro Ser Val Phe Ile Phe Pro Pro Ser
    130                 135                 140

Asp Glu Gln Leu Lys Ser Gly Thr Ala Ser Val Val Cys Leu Leu Asn
145                 150                 155                 160

Asn Phe Tyr Pro Arg Glu Ala Lys Val Gln Trp Lys Val Asp Asn Ala
                165                 170                 175

Leu Gln Ser Gly Asn Ser Gln Glu Ser Val Thr Glu Gln Asp Ser Lys
            180                 185                 190

Asp Ser Thr Tyr Ser Leu Ser Ser Thr Leu Thr Leu Ser Lys Ala Asp
        195                 200                 205

Tyr Glu Lys His Lys Leu Tyr Ala Cys Glu Val Thr His Gln Gly Leu
    210                 215                 220

Ser Ser Pro Val Thr Lys Ser Phe Asn Arg Gly Glu Cys
225                 230                 235


<210> SEQ ID NO 2
<211> LENGTH: 469
<212> TYPE: PRT
<213> ORGANISM: Artificial Sequence
<220> FEATURE:
<223> OTHER INFORMATION: Heavy chain of the humanized anti-CXCR2
      monoclonal antibody

<400> SEQUENCE: 2

Met Gly Arg Leu Thr Ser Ser Phe Leu Leu Leu Ile Val Pro Ala Tyr
1               5                   10                  15

Val Leu Ser Gln Ile Thr Leu Lys Glu Ser Gly Pro Thr Leu Val Lys
            20                  25                  30

Pro Thr Gln Thr Leu Thr Leu Thr Cys Thr Phe Ser Gly Phe Ser Leu
        35                  40                  45

Arg Thr Ser Gly Met Gly Val Gly Trp Ile Arg Gln Pro Pro Gly Lys
    50                  55                  60

Ala Leu Glu Trp Leu Ala His Ile Trp Trp Asp Asp Asp Lys Arg Tyr
65                  70                  75                  80

Lys Pro Asp Leu Lys Ser Arg Leu Thr Ile Thr Lys Asp Thr Ser Lys
                85                  90                  95

Asn Gln Val Val Leu Thr Met Thr Asn Met Asp Pro Val Asp Thr Ala
            100                 105                 110

Thr Tyr Tyr Cys Ala Arg Leu Gly Leu Arg Leu Arg Thr Met Asp Tyr
```

```
        115                 120                 125

Trp Gly Gln Gly Thr Leu Val Thr Val Ser Ser Ala Ser Thr Lys Gly
    130                 135                 140

Pro Ser Val Phe Pro Leu Ala Pro Ser Ser Lys Ser Thr Ser Gly Gly
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Ser Leu Gly Thr Gln Thr Tyr Ile Cys Asn Val
    210                 215                 220

Asn His Lys Pro Ser Asn Thr Lys Val Asp Lys Lys Val Glu Pro Lys
225                 230                 235                 240

Ser Cys Asp Lys Thr His Thr Cys Pro Pro Cys Pro Ala Pro Glu Leu
                245                 250                 255

Leu Gly Gly Pro Ser Val Phe Leu Phe Pro Pro Lys Pro Lys Asp Thr
            260                 265                 270

Leu Met Ile Ser Arg Thr Pro Glu Val Thr Cys Val Val Val Asp Val
        275                 280                 285

Ser His Glu Asp Pro Glu Val Lys Phe Asn Trp Tyr Val Asp Gly Val
    290                 295                 300

Glu Val His Asn Ala Lys Thr Lys Pro Arg Glu Glu Gln Tyr Asn Ser
305                 310                 315                 320

Thr Tyr Arg Val Val Ser Val Leu Thr Val Leu His Gln Asp Trp Leu
                325                 330                 335

Asn Gly Lys Glu Tyr Lys Cys Lys Val Ser Asn Lys Ala Leu Pro Ala
            340                 345                 350

Pro Ile Glu Lys Thr Ile Ser Lys Ala Lys Gly Gln Pro Arg Glu Pro
        355                 360                 365

Gln Val Tyr Thr Leu Pro Pro Ser Arg Asp Glu Leu Thr Lys Asn Gln
    370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
                405                 410                 415

Pro Pro Val Leu Asp Ser Asp Gly Ser Phe Phe Leu Tyr Ser Lys Leu
            420                 425                 430

Thr Val Asp Lys Ser Arg Trp Gln Gln Gly Asn Val Phe Ser Cys Ser
        435                 440                 445

Val Met His Glu Ala Leu His Asn His Tyr Thr Gln Lys Ser Leu Ser
    450                 455                 460

Leu Ser Pro Gly Lys
465


<210> SEQ ID NO 3
<211> LENGTH: 16
<212> TYPE: PRT
<213> ORGANISM: Artificial Sequence
<220> FEATURE:
<223> OTHER INFORMATION: CDR1 of VL

<400> SEQUENCE: 3

Arg Ser Ser Leu Ser Leu Val His Ser Asn Gly Asp Thr Tyr Leu His
```

1 5 10 15

<210> SEQ ID NO 4
<211> LENGTH: 7
<212> TYPE: PRT
<213> ORGANISM: Artificial Sequence
<220> FEATURE:
<223> OTHER INFORMATION: CDR2 of VL

<400> SEQUENCE: 4

Lys Val Ser Asn Arg Phe Ser
1 5

<210> SEQ ID NO 5
<211> LENGTH: 8
<212> TYPE: PRT
<213> ORGANISM: Artificial Sequence
<220> FEATURE:
<223> OTHER INFORMATION: CDR3 of VL

<400> SEQUENCE: 5

Ser Gln Ser Thr His Val Pro Thr
1 5

<210> SEQ ID NO 6
<211> LENGTH: 7
<212> TYPE: PRT
<213> ORGANISM: Artificial Sequence
<220> FEATURE:
<223> OTHER INFORMATION: CDR1 of VH

<400> SEQUENCE: 6

Thr Ser Gly Met Gly Val Gly
1 5

<210> SEQ ID NO 7
<211> LENGTH: 16
<212> TYPE: PRT
<213> ORGANISM: Artificial Sequence
<220> FEATURE:
<223> OTHER INFORMATION: CDR2 of VH

<400> SEQUENCE: 7

His Ile Trp Trp Asp Asp Asp Lys Arg Tyr Lys Pro Asp Leu Lys Ser
1 5 10 15

<210> SEQ ID NO 8
<211> LENGTH: 10
<212> TYPE: PRT
<213> ORGANISM: Artificial Sequence
<220> FEATURE:
<223> OTHER INFORMATION: CDR3 of VH

<400> SEQUENCE: 8

Leu Gly Leu Arg Leu Arg Thr Met Asp Tyr
1 5 10

<210> SEQ ID NO 9
<211> LENGTH: 111
<212> TYPE: PRT
<213> ORGANISM: Artificial Sequence
<220> FEATURE:
<223> OTHER INFORMATION: light chain variable region of the humanized anti-CXCR2 monoclonal antibody

<400> SEQUENCE: 9

Asp Ile Val Met Thr Gln Thr Pro Leu Ser Leu Ser Val Thr Pro Gly

-continued

```
1               5                   10                  15

Gln Pro Ala Ser Ile Ser Cys Arg Ser Ser Leu Ser Leu Val His Ser
            20                  25                  30

Asn Gly Asp Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Val Pro Thr Phe Gly Gln Gly Thr Lys Leu Glu Ile Lys
            100                 105                 110


<210> SEQ ID NO 10
<211> LENGTH: 120
<212> TYPE: PRT
<213> ORGANISM: Artificial Sequence
<220> FEATURE:
<223> OTHER INFORMATION: heavy chain variable region of the humanized
      anti-CXCR2 monoclonal antibody

<400> SEQUENCE: 10

Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Arg Thr Ser
            20                  25                  30

Gly Met Gly Val Gly Trp Ile Arg Gln Pro Pro Gly Lys Ala Leu Glu
        35                  40                  45

Trp Leu Ala His Ile Trp Trp Asp Asp Asp Lys Arg Tyr Lys Pro Asp
    50                  55                  60

Leu Lys Ser Arg Leu Thr Ile Thr Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Leu Gly Leu Arg Leu Arg Thr Met Asp Tyr Trp Gly Gln
            100                 105                 110

Gly Thr Leu Val Thr Val Ser Ser
        115                 120


<210> SEQ ID NO 11
<211> LENGTH: 20
<212> TYPE: PRT
<213> ORGANISM: Artificial Sequence
<220> FEATURE:
<223> OTHER INFORMATION: antigen peptide of CXCR2

<400> SEQUENCE: 11

Met Glu Asp Phe Asn Met Glu Ser Asp Ser Glu Glu Asp Phe Trp Lys
1               5                   10                  15

Gly Glu Asp Leu
            20
```

ANTI-CXCR2 ANTIBODIES AND USES THEREOF

This application is a national stage application, filed under 35 U.S.C. § 371, of the International Patent Application No. PCT/CN2022/088964, filed on Apr. 25, 2022, which claims the benefit of the U.S. Provisional Application No. 63/179,554, filed on Apr. 26, 2021, all of which are incorporated by reference herein in their entirety. This application also contains a Sequence Listing in a computer readable form, the file name is 4152-KMU-SequenceListing, created on Aug. 22, 2023, the size is 12 KB, which is incorporated herein by reference.

FIELD OF THE INVENTION

The present invention relates to anti-CXCR2 antibodies that recognize CXCR2 and inhibit the activity of CXCR2 and the use of the anti-CXCR2 antibodies in the treatment of pancreatic cancer and leukemia.

DESCRIPTION OF PRIOR ART

Chemokines are crucial signaling molecules that play important roles in immune modulation, proliferation, angiogenesis and progression of multiple tumor types such as melanoma, glioblastoma, non-small cell lung carcinoma, prostrate, pancreatic, hepatocellular and renal carcinoma. Emerging evidence strongly suggested that C-X-C chemokine receptor 2 (CXCR2) is a critical target for cancer therapy. First, pathological investigation showed that over-expression of CXCR2 and/or its ligands (CXCL1, 2, 3, 5, 6, 7 and 8) is frequently found in human cancers. Second, meta-analysis indicated that upregulation of CXCR2 and its ligands (especially CXCL8, also known as IL-8) is a poor prognostic factor in solid tumors. Third, some newly developed CXCR2 inhibitors showed potent anti-cancer activity in preclinical studies. However, the development of CXCR2-specific chemical inhibitors faces some difficulties due to the high structural similarity of CXCR2 with another closely related receptor CXCR1. Two anti-IL-8 blocking antibodies ABX-IL8 and HuMAX-IL8 have been developed in the past decade. However, their therapeutic effect is significantly restrained because CXCR2 could be activated by seven ligands and neutralization of IL-8 alone could not completely inhibit the CXCR2 signaling. Therapeutic intervention to disrupt the CXCR2/CXCL8 interaction and inhibit subsequent downstream signal transduction could offer a treatment paradigm for various human diseases.

DETAILED DESCRIPTION OF THE INVENTION

To generate the anti-CXCR2 antibodies by targeting a conserved functional epitope, the present invention designs a novel human CXCR2 antigen peptide immunization strategy. Therefore, the immunization strategy of the present invention generates high-affinity anti-CXCR2 monoclonal antibodies. The present invention then generates a novel humanized anti-CXCR2 monoclonal antibody. This anti-CXCR2 monoclonal antibody shows high binding affinity to various CXCR2 expressing human cancer cells at sub-nanomolar level. Functional assay demonstrates that the humanized anti-CXCR2 monoclonal antibody binds human pancreatic cancer cells and leukemia cells and suppresses their proliferation in culture. Animal studies also show that the humanized anti-CXCR2 monoclonal antibody can suppress the growth of pancreatic cancer and leukemia in vivo. This humanized anti-CXCR2 monoclonal antibody can be used for the treatment of pancreatic cancer and leukemia.

As used herein, the term "a" or "an" are employed to describe elements and components of the present invention. This is done merely for convenience and to give a general sense of the present invention. This description should be read to include one or at least one and the singular also includes the plural unless it is obvious that it is meant otherwise.

The present invention provides an isolated antibody that binds to chemokine C-X-C motif receptor 2 (CXCR2), comprising a light chain and a heavy chain, wherein the variable region of the light chain comprises a CDR-L1 having the sequence of SEQ ID NO: 3, a CDR-L2 having the sequence of SEQ ID NO: 4 and a CDR-L3 having the sequence of SEQ ID NO: 5, and the variable region of the heavy chain comprises a CDR-H1 having the sequence of SEQ ID NO: 6, a CDR-H2 having the sequence of SEQ ID NO: 7 and a CDR-H3 having the sequence of SEQ ID NO: 8.

The term "antibody" is used in the broadest sense and specifically covers monoclonal antibodies, polyclonal antibodies, multispecific antibodies, and antibody fragments so long as they exhibit the desired biological activity, that is, to specifically bind to an antigen when it preferentially recognizes its target antigen in a complex mixture of proteins and/or other molecules.

An "antibody" refers to a glycoprotein comprising at least two heavy (H) chains and two light (L) chains inter-connected by disulfide bonds, or an antigen binding portion thereof. Each heavy chain is comprised of a heavy chain variable region (abbreviated herein as VH) and a heavy chain constant region. Each light chain is comprised of a light chain variable region (abbreviated herein as VL) and a light chain constant region. The VH and VL regions can be further subdivided into regions of hypervariability, termed complementarity determining region (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (Clq) of the classical complement system.

As used herein, the term "complementarity determining region" (syn. CDR; i.e., CDR1, CDR2, and CDR3) refers to the amino acid residues of an antibody variable region the presence of which are major contributors to specific antigen binding. Each variable region (VH or VL) typically has three CDRs identified as CDR1, CDR2 and CDR3. The CDRs of VH are also referred to herein as CDR-H1, CDR-H2 and CDR-H3, respectively, wherein CDR-H1 corresponds to CDR1 of VH, CDR-H2 corresponds to CDR2 of VH and CDR-H3 corresponds to CDR3 of VH. Likewise, the CDRs of VL are referred to herein as CDR-L1, CDR-L2 and CDR-L3, respectively, wherein CDR-L1 corresponds to CDR1 of VL, CDR-L2 corresponds to CDR2 of VL and CDR-L3 corresponds to CDR3 of VL.

An "isolated" antibody is one which has been identified and separated and/or recovered from a component of its nature environment. Containment components of its nature environment are materials which would interfere with therapeutic uses of the antibody of this invention, and may include enzymes, hormones, and other proteinaceous or non-proteinaceous solutes. Isolated antibody includes the antibody in situ within recombinant cells. Ordinarily, isolated antibody will be prepared by at least one purification step.

The term "monoclonal antibody" as used herein refers to an antibody obtained from a population of substantially homogeneous antibodies, and is not to be constructed as requiring production of the antibody by any particular method. In contrast to polyclonal antibodies which typically include different antibodies directed to different epitopes, each monoclonal antibody is directed against a single determinant (i.e., epitope) on the antigen. The monoclonal antibodies of the present disclosure may be made by the hybridoma method or by recombinant DNA methods. The monoclonal antibodies herein specifically include "chimeric" or "recombinant" antibodies, in which a portion of the heavy and/or light chain is identical with or homologous to corresponding sequences in antibodies derived from a particular species or belonging to a antibody class or subclass, while the remainder of the chain identical with or homologous to corresponding sequences in antibodies derived from another species or belonging to another antibody class or subclass, as well as fragments of such antibodies, as long as they exhibit the desired biological activity.

"Humanized" forms of non-human (e.g., murine) antibodies are chimeric antibodies which contain minimal sequence derived from non-human immunoglobulin. Humanized antibodies are human immunoglobulins in which hypervariable region residues are replaced by hypervariable region residues from a non-human species such as mouse, rat, rabbit, or non-human primate having the desired specificity or affinity. In some instances, Fv framework region (FR) residues of the human immunoglobulin are replaced by corresponding non-human residues. In general, the humanized antibody will comprise substantially all of at least one, and typically two, variable regions, in which all or substantially all of the FR regions are those of a human immunoglobulin sequence. The humanized antibody may optionally comprise at least a portion of an immunoglobulin constant region (Fc), typically that of a human immunoglobulin.

In one embodiment, the light chain of the isolated antibody comprises the amino caid sequence of SEQ ID NO: 1, and the heavy chain of the isolated antibody comprises the amino caid sequence of SEQ ID NO: 2.

In another embodiment, the VL of the isolated antibody comprises the amino caid sequence of SEQ ID NO: 9, and the VH of the isolated antibody comprises the amino caid sequence of SEQ ID NO: 10.

In the present invention, the isolated antibody is able to bind to or specifically bind to CXCR2 and inhibits CXCR2 activity. The CXCR2 activity that may be inhibited by the isolated antibody of the present invention includes: ligand binding to CXCR2; ligand induced conformational change of CXCR2; CXCR2 activation; G protein activation; CXCR2 mediated cell signaling pathway; CXCR2 mediated tumor cell growth; and/or CXCR2 mediated leukocyte (e.g. neutrophil, eosinophil, mast cell or T cell). In one embodiment, the isolated antibody reduces the affinity between a ligand and CXCR2. In a preferred embodiment, the ligand comprises IL-8.

CXCR2 is also known as C-X-C motif chemokine receptor 2 (CD182; IL8R2; IL8RA; IL8RB; CMKAR2; CDw128b). CXCR2 is a G protein-coupled receptor (GPCR) that is expressed on many different cells and tissues, including neutrophils, mast cells, $CD8^+$ T cells, epithelial, endothelial, smooth muscle, and a variety of cell types in the central nervous system. Several high-affinity ligands have been identified, CXCL1 (growth-related oncogene a [GRO-α]), CXCL8 (interleukin-8), and CXCL5 (ENA-78) as well as lower affinity ligands CXCL2 (GRO-β), CXCL3 (GRO-γ), CXCL6 (GCP-2), and CXCL7 (NAP-2).

The term "CXCR2" as provided herein includes any of the C-X-C motif chemokine receptor 2 (CXCR2) protein naturally occurring forms, homologs or variants that maintain the activity of CXCR2 (e.g., within at least 50%, 80%, 90%, 95%, 96%, 97%, 98%, 99% or 100% activity compared to the native protein). In some embodiments, variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring form. In embodiments, the CXCR2 protein is the protein as identified by the UniProt sequence reference P25025, homolog or functional fragment thereof.

The present invention also provides a method for treating a subject suffering from a pancreatic cancer, comprising administering to the subject with pancreatic cancer a composition comprising an antibody that binds to chemokine C-X-C motif receptor 2 (CXCR2), wherein the antibody comprises a light chain and a heavy chain, wherein the variable region of the light chain comprises a CDR-L1 having the sequence of SEQ ID NO: 3, a CDR-L2 having the sequence of SEQ ID NO: 4 and a CDR-L3 having the sequence of SEQ ID NO: 5, and the variable region of the heavy chain comprises a CDR-H1 having the sequence of SEQ ID NO: 6, a CDR-H2 having the sequence of SEQ ID NO: 7 and a CDR-H3 having the sequence of SEQ ID NO: 8.

In addition, the present invention further provides a use of a composition in the preparation of a drug for treating pancreatic cancers, wherein the composition comprises an antibody that binds to chemokine C-X-C motif receptor 2 (CXCR2), wherein the antibody comprises a light chain and a heavy chain, wherein the variable region of the light chain comprises a CDR-L1 having the sequence of SEQ ID NO: 3, a CDR-L2 having the sequence of SEQ ID NO: 4 and a CDR-L3 having the sequence of SEQ ID NO: 5, and the variable region of the heavy chain comprises a CDR-H1 having the sequence of SEQ ID NO: 6, a CDR-H2 having the sequence of SEQ ID NO: 7 and a CDR-H3 having the sequence of SEQ ID NO: 8.

As used herein, the term "treating" refers to any improvements of a disease or illness (also refers to inhibition of the disease or amelioration of the appearance, extent or severity of at least one of its clinical symptoms).

As used herein, the term "subject" refers to an animal. In a preferred embodiment, the subject refers to a mammal. In a more preferred embodiment, the subject refers to a human.

In one embodiment, the antibody inhibits the cancer cell proliferation of the pancreatic cancer. In a preferred embodiment, the antibody inhibits the tumor growth of the pancreatic cancer.

As used herein, the term "inhibit" in reference to cell proliferation (e.g., cancer cell proliferation) means negatively affecting (e.g., decreasing proliferation) or killing the cell. In some embodiments, inhibition refers to reduction of a disease or symptoms of disease (e.g., cancer, cancer cell proliferation). Thus, inhibition includes, at least in part, partially or totally blocking stimulation, decreasing, preventing, or delaying activation, or inactivating, desensitizing, or down-regulating signal transduction or enzymatic activity or the amount of a protein.

The present invention also provides a method for treating a subject suffering from a leukemia, comprising administering to the subject with leukemia a composition comprising an antibody that binds to chemokine C-X-C motif receptor 2 (CXCR2), wherein the antibody comprises a light chain and a heavy chain, wherein the variable region of the light chain comprises a CDR-L1 having the sequence of SEQ ID NO: 3, a CDR-L2 having the sequence of SEQ ID NO: 4 and a CDR-L3 having the sequence of SEQ ID NO: 5, and the variable region of the heavy chain comprises a CDR-H1 having the sequence of SEQ ID NO: 6, a CDR-H2 having the sequence of SEQ ID NO: 7 and a CDR-H3 having the sequence of SEQ ID NO: 8.

In addition, the present invention further provides a use of a composition in the preparation of a drug for treating leukemia, wherein the composition comprises an antibody that binds to chemokine C-X-C motif receptor 2 (CXCR2), wherein the antibody comprises a light chain and a heavy chain, wherein the variable region of the light chain comprises a CDR-L1 having the sequence of SEQ ID NO: 3, a CDR-L2 having the sequence of SEQ ID NO: 4 and a CDR-L3 having the sequence of SEQ ID NO: 5, and the variable region of the heavy chain comprises a CDR-H1 having the sequence of SEQ ID NO: 6, a CDR-H2 having the sequence of SEQ ID NO: 7 and a CDR-H3 having the sequence of SEQ ID NO: 8.

In another embodiment, the leukemia comprises acute lymphoblastic leukemia (ALL), acute myeloid leukemia (AML), chronic lymphocytic leukemia (CLL), chronic myeloid leukemia (CML), chronic myelomonocytic leukemia (CMML) or hairy cell leukemia (HCL).

In one embodiment, the antibody inhibits the leukocyte proliferation of the leukemia. In a preferred embodiment, the leukocyte comprises neutrophils, lymphocyte, monocytes, eosinophils or basophils. In a preferred embodiment, the leukocyte comprises mast cells.

In one embodiment, the subject suffering from the pancreatic cancer or the leukemia has previously received, is concurrently receiving, or will subsequently receive immunotherapy.

In some examples, the composition comprising the antibody of the present invention can be administered via any suitable enteral route or parenteral route of administration. The term "enteral route" of administration refers to the administration via any part of the gastrointestinal tract. Examples of enteral routes include oral, mucosal, buccal, and rectal route, or intragastric route. "Parenteral route" of administration refers to a route of administration other than enteral route. Examples of parenteral routes of administration include intravenous, intramuscular, intradermal, intraperitoneal, intratumor, intravesical, intraarterial, intrathecal, intracapsular, intraorbital, intracardiac, transtracheal, intraarticular, subcapsular, subarachnoid, intraspinal, epidural and intrasternal, subcutaneous, or topical administration. The therapeutic agents and compositions of the disclosure can be administered using any suitable method, such as by oral ingestion, nasogastric tube, gastrostomy tube, injection, infusion, implantable infusion pump, and osmotic pump. The suitable route and method of administration may vary depending on a number of factors such as the specific therapeutic agent being used, the rate of absorption desired, specific formulation or dosage form used, type or severity of the disorder being treated, the specific site of action, and conditions of the patient, and can be readily selected by a person skilled in the art.

In one embodiment, the composition further comprises a pharmaceutically acceptable carrier. The term "pharmaceutically acceptable carrier" refers to any inactive substance that is suitable for use in a formulation for the delivery of a therapeutic agent. A carrier may be an antiadherent, binder, coating, disintegrant, filler or diluent, preservative (such as antioxidant, antibacterial, or antifungal agent), sweetener, absorption delaying agent, wetting agent, emulsifying agent, buffer, and the like. Examples of suitable pharmaceutically acceptable carriers include water, ethanol, polyols (such as glycerol, propylene glycol, polyethylene glycol, and the like), dextrose, vegetable oils (such as olive oil), saline, buffer, buffered saline, and isotonic agents such as sugars, polyalcohols, sorbitol, and sodium chloride.

In the present invention, the composition comprises a therapeutically effective amount of the antibody of the present invention. The phrase "therapeutically effective amount" is used herein to mean an amount sufficient to cause an improvement in a clinically significant condition in the subject, or delays or minimizes or mitigates one or more symptoms associated with the disease or disorder, or results in a desired beneficial change of physiology in the subject.

In one embodiment, the therapeutically effective amount of the antibody ranges from 1-100 mg/kg of body weight of the subject. In a preferred embodiment, the therapeutically effective amount of the antibody ranges from 5-70 mg/kg of body weight of the subject. In a more preferred embodiment, the therapeutically effective amount of the antibody ranges from 10-50 mg/kg of body weight of the subject.

In one embodiment, the antibody is administered twice per week. In a preferred embodiment, the antibody is administered weekly for at least three weeks. In a more preferred embodiment, the antibody is administered weekly for at least four weeks.

BRIEF DESCRIPTION OF THE DRAWINGS

FIG. 1 shows the generation of functionally active monoclonal antibodies against human CXCR2.

FIG. 3 shows characterization of the binding affinity of humanized anti-CXCR2 monoclonal antibody (anti-CXCR2 mAb) in vitro and in cells.

FIG. 4 shows the inhibition of CXCR2-mediated signal transduction by humanized anti-CXCR2 mAb (NICR2-5).

FIG. 7 shows that the treatment of humanized anti-CXCR2 mAb (NICR2-5) inhibits the proliferation HMC-1 leukemia cells in blood and bone marrow in SCID mice. HMC-1 leukemia cells are intravenously injected into immune-deficient SCID mice. One week later, normal IgG1 or anti-CXCR2 mAb is given at a dose of 30 mg/kg twice per week. The mice are treated with antibody for 7 times and were sacrificed at day 27 after cancer cell injection. Blood and bone marrow of the mice are harvested and the percentage of human leukemia cells detected by hCD68 is investigated by flow cytometric analysis.

EXAMPLES

The present invention may be implemented in many different forms and should not be construed as limited to the examples set forth herein. The described examples are not limited to the scope of the present invention as described in the claims.

Figure 1A:
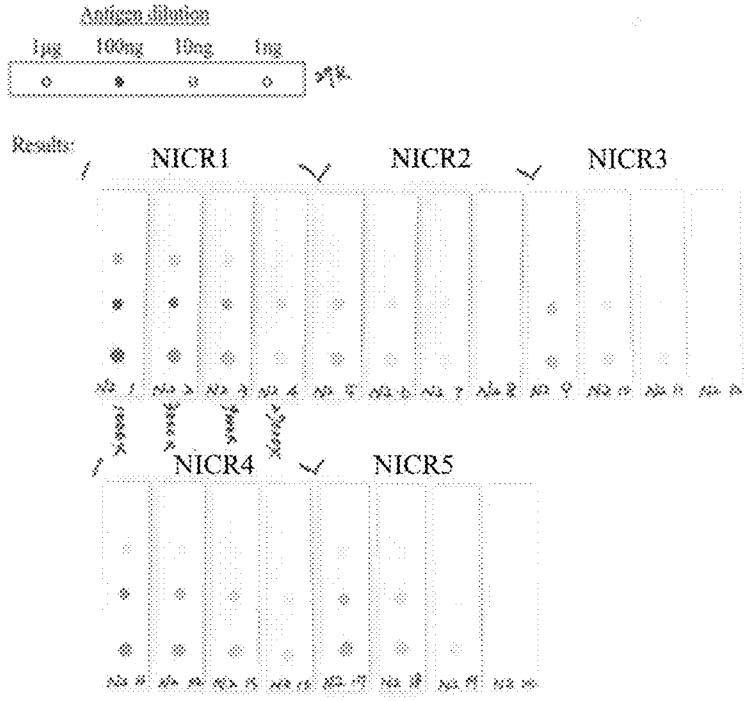
FIG. 1A shows that the Dot-blot results reveals that human CXCR2 cross-reactive hybridoma supernatants. The dose of antigen (NICR1, NICR2, NICR3, NICR4 and NICR5) dilution is 1 μg, 100 ng, 10 ng and 1 ng.

Production of Anti-Human CXCR2 Monoclonal Antibodies by an Antigen Immunization Strategy The IL-8-CXCR1/2 signaling axis plays a crucial role in various human diseases, it is not surprising that this signaling pathway becomes an important target for drug development. The present invention immunized the mice by specific CXCR2 antigen and generated hybridoma clones which produced high-affinity monoclonal antibodies. The sequence of antigen peptide (NICR2 peptide) is MEDFNMESDSEEDFWKGEDL (SEQ ID No. 11)-C-Ovalbumin (C-Ovalbumin indicated that the peptide was conjugated with Ovalbumin at the C-terminal of the peptide). After immunization for 6 times, the splenocytes of the immunized mice were fused with immortalized myeloma cells to generate hybridoma cells by standard protocols. The hybridoma clones with the highest CXCR2 specific antibody titers, determined by Dot-blot assay, were used and selected for antibody production and testing. Dot-blot assays were performed to investigate the affinity of antibodies against five different antigen peptide (NICR1, NICR2, NICR3, NICR4 and NICR5) at varying concentrations (1 μg, 100 ng, 10 ng and 1 ng) (FIG. 1A). The monoclonal antibody in hybridoma supernatants was purified by affinity column and was used for enzyme-linked immunosorbent assay (ELISA) to check the binding affinity and specificity. In ELISA assay, the present invention coated with plates with antigen peptide (NICR2 peptide) (5 μg/ml). The peptide-coated plates were incubated with 1% of bovine serum albumin (BSA) 1 h at room temperature to block non-specific binding and were incubated with different concentrations of purified monoclonal antibody (0, 15.625, 31.25, 62.5, 125, 250, 500, 1000 ng/ml) at 4° C. overnight. After washing by phosphate-buffered saline (PBS), anti-mouse secondary antibody (10,000× dilution) was added and incubated at room temperature for 2 h. The developing substrate (3,3',5,5'-Tetramethylbenzidine) was added and incubated at room temperature for 20 min. The reaction was stopped by stop solution and the absorbance at 450 nm was detected by spectrometry.

Generation of Humanized Anti-CXCR2 Monoclonal Antibody

Figure 1B:
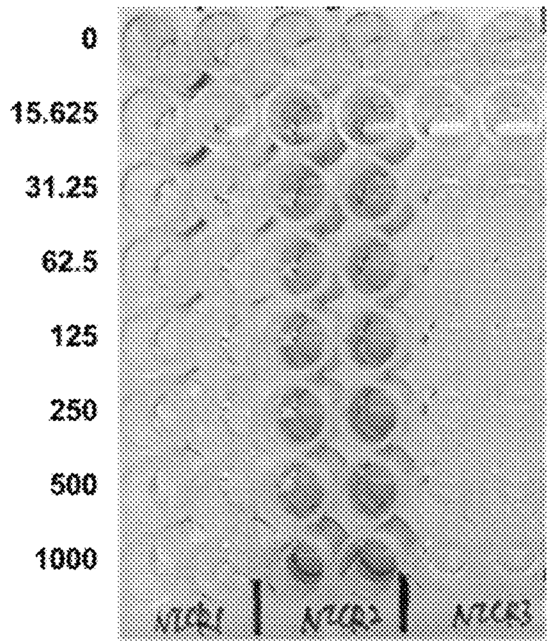
FIG. 1B shows that the enzyme-linked immunosorbent assay shows the specific binding of NICR2-5 monoclonal antibody (with different concentrations) purified from hybridoma supernatants interacted specifically with the CXCR2 antigen peptide (named as NICR2 peptide). The sequence of antigen peptide is MEDFNMESDSEEDFWKGEDL (SEQ ID No. 11).
Figure 2:
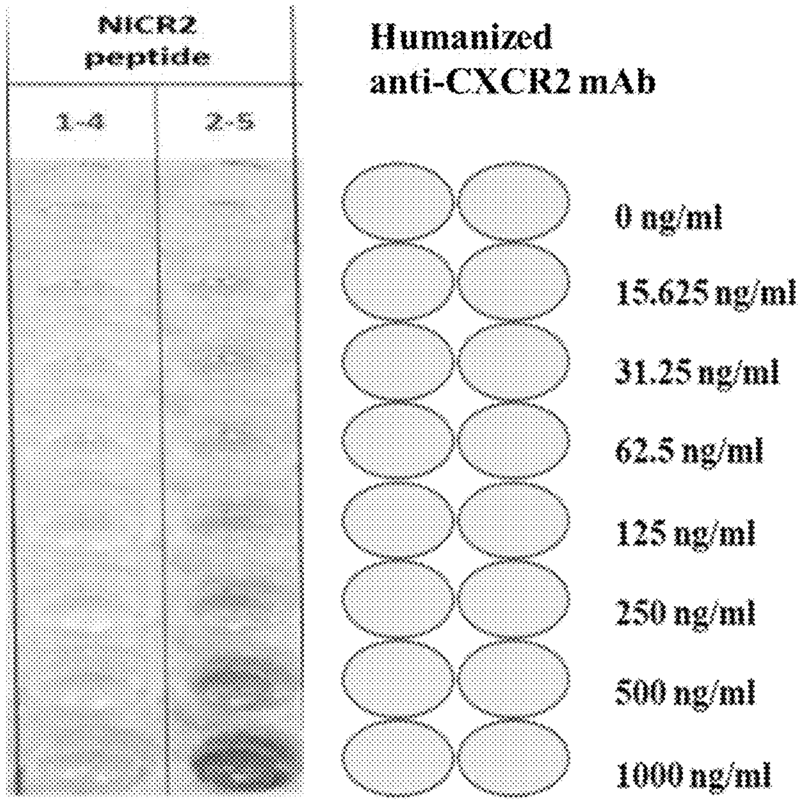
FIG. 2 shows that the specificity and binding affinity of the humanized anti-CXCR2 monoclonal antibody (anti-CXCR2 mAb) are not altered after humanization.

Five mouse cross-reactive hybridomas were isolated. Notably, the monoclonal antibody (NICR2-5 monoclonal antibody) from one of these hybridomas showed strong binding with antigen peptide (NICR2 peptide) and did not have cross-reactivity comparable to non-specific peptides (NICR1 and NICR3) as determined by ELISA assay (FIG. 1B). The hybridoma with highest binding affinity was sequenced by next-generation sequencing (NGS) to identify the antibody sequence. The results of five clones sequenced showed more than 99% sequence identity, suggesting the hybridoma contains one single monoclonal antibody clone. The present invention then did antibody humanization by cloning the CDR regions of light chain and heavy chain into human IgG1 vector. Therefore, the present invention prepared the humanized anti-CXCR2 monoclonal antibody (anti-CXCR2 mAb) comprising a light chain and a heavy chain, in which the light chain comprised the amino caid sequence of SEQ ID NO: 1, and the heavy chain comprised the amino caid sequence of SEQ ID NO: 2. In addition, the VL of the anti-CXCR2 mAb comprised the sequences of SEQ ID No: 9 and the VH of the anti-CXCR2 mAb comprised the sequences of SEQ ID NO: 10. Furthermore, the VL of the anti-CXCR2 mAb comprised CDR sequences of SEQ ID Nos: 3-5 and the VH of the anti-CXCR2 mAb comprised CDR sequences of SEQ ID NOs: 6-8. FIG. 2 demonstrated strong binding of the humanized anti-CXCR2 mAb to antigen peptide and no non-specific cross-reactivity was found.

Figure 3A:
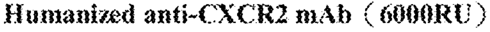
FIG. 3A shows that the binding affinity of humanized anti-CXCR2 mAb (NICR2-5) to the CXCR2 antigen peptide (NICR2 peptide) is investigated by surface plasmon resonance (SPR) Biacore technique. Equilibrium affinity and rate constants derived from a Langmuir 1:1 binding kinetic analysis. The interactions between the humanized anti-CXCR2 mAb and the CXCR2 antigen peptide (NICR2 peptide) were detected by using SPR. The humanized anti-CXCR2 mAb flowed through the CXCR2 antigen peptide (NICR2 peptide) at the indicated concentrations. Data were corrected for nonspecific background binding. All data are representative of three independent experiments.
Figure 3A:
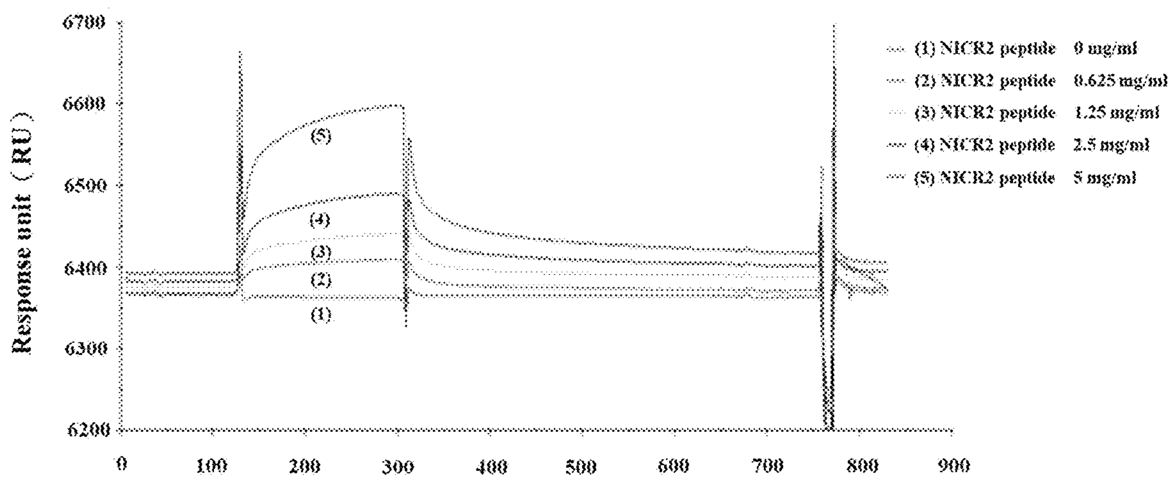
Figure 3B:
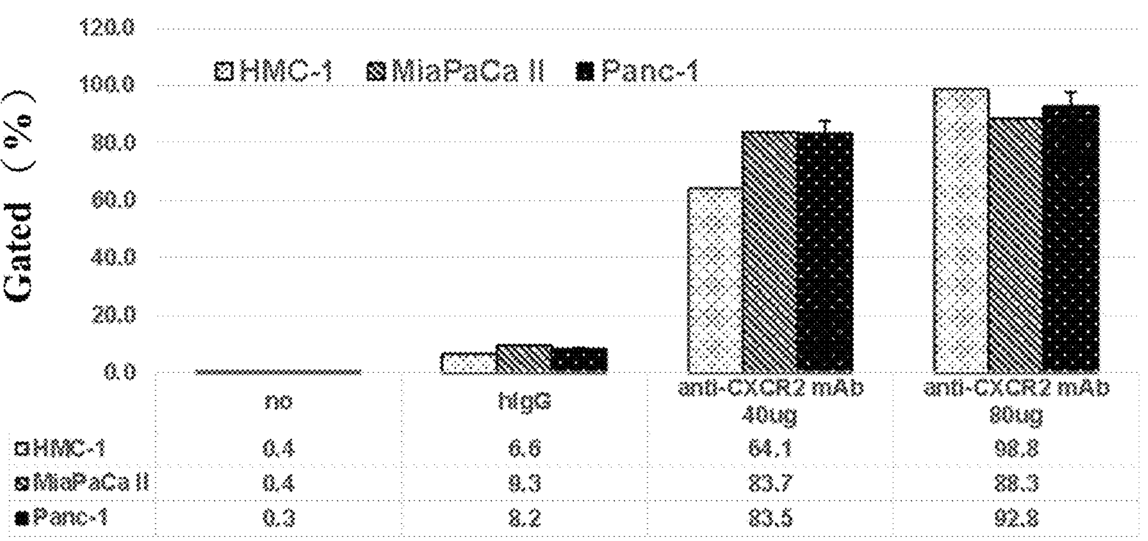
FIG. 3B shows the binding of humanized anti-CXCR2 mAb to human mast leukemia cell line (HMC-1), pancreatic cancer cells (MiaPaca-2 and Panc-1) in the absence or presence of varying concentrations (0 μg, 40 μg and 80 μg) of the antibodies. Data shown is representative of 3 independent experiments.

Characterization of the Binding of Anti-CXCR2 mAb (NICR2-5) In Vitro and in Cells The binding affinity of the humanized anti-CXCR2 monoclonal antibody (NICR2-5) was further investigated by surface plasmon resonance (SPR) Biacore technique. The estimated KD is 0.3 nM (FIG. 3A), indicating the strong binding. The binding of the humanized anti-CXCR2 mAb (NICR2-5) to cell surface receptor was analyzed by flow cytometry. Control IgG1 or humanized anti-CXCR2 mAb (NICR2-5) were conjugated with Alexa Fluor-488 fluorescent dye. Cancer cells were fixed with 3.5% formaldehyde for 15 min at room temperature. Fixed cells were incubated with fluorescent dye-conjugated IgG1 (80 μg/ml), or different concentrations of humanized anti-CXCR2 mAb (NICR2-5) (0, 40, 80 μg/ml) at 4° ° C. for 1 h. Cells were washed with phosphate-buffered saline (PBS) three times and subjected to flow cytometric analysis by using Attune NxT Flow Cytometer. The data of the present invention demonstrated that the humanized anti-CXCR2 mAb (NICR2-5) specifically bound to the CXCR2 receptor on human mast cell leukemia HMC-1 and human pancreatic cancer cells in a-dose-dependently manner (FIG. 3B).

Figure 4A:
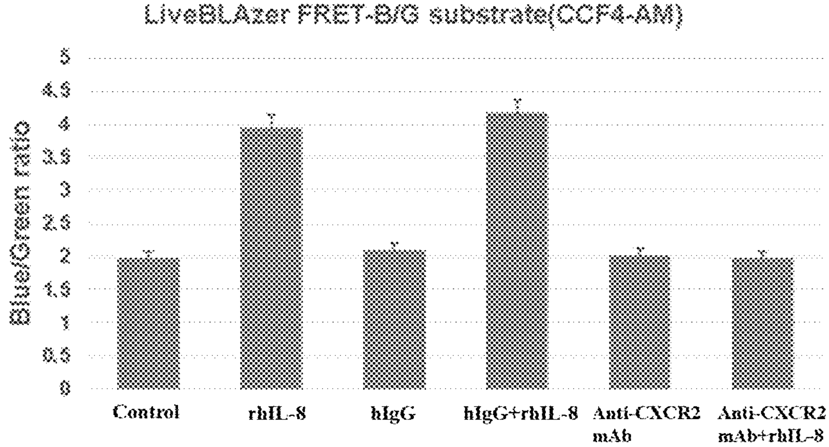
FIG. 4A shows that U2OS reporter cells with CXCR2 expression are treated with control IgG, anti-CXCR2 mAb (100 μg/ml), interleukin-8 (rhIL-8) (300 ng/ml) for 16 h. The increase of blue/green fluorescent intensity ratio indicated the enhancement of the binding of beta-arrestin to CXCR2 receptor is measured. The data are representative of three independent experiments.
Figure 4B:
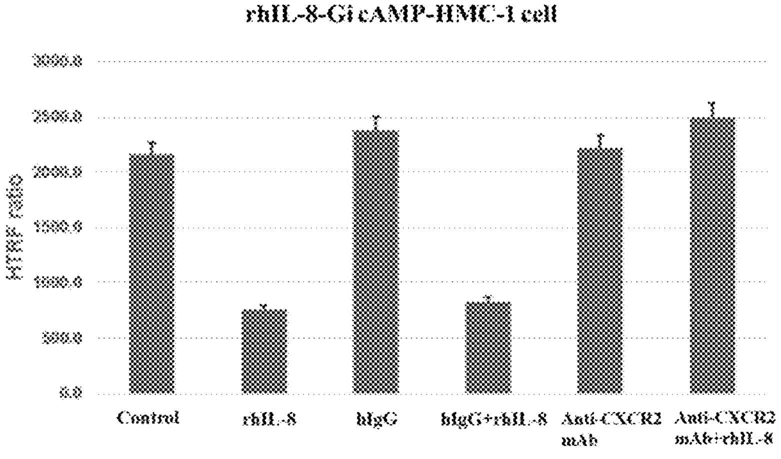
FIG. 4B shows that the human mast leukemia cell line (HMC-1) and pancreatic cancer cells (MiaPaca-2) are treated as described above. Intracellular cAMP level was measured by using cAMP assay kit (CIS-BIO).

Humanized Anti-CXCR2 mAb (NICR2-5) Inhibits CXCR2 Receptor-Mediated Signal Transduction Pathway CXCR2 is a G protein-coupled receptor. After ligand stimulation, CXCR2 will recruit beta-arrestin and activate Gi protein to inhibit adenylate cyclase which leads to reduction of intracellular CAMP level. To study the interaction between CXCR2 and beta-arrestin, the present invention used Tango GPCR Assay System developed by Thermo Fisher company. Tango™-beta-arrestin-UAS-bla U2OS cells were transfected with CXCR2 expression vector to establish CXCR2-expressing stable clones. Cells were seeded at the density of 10,000 cells/well in 96-well plates. After 24 h, cells were treated with different combinations of antibody and IL-8 for 16 h. After extensively washing, cells were incubated with LiveBLAzer™-FRET B/G substrate for 2 h at room temperature. The fluorescent intensities were examined by using Excitation filter: 409/20 nm and Emission filter 460/40 nm and 530/30 nm to detect green and blue fluorescence separately. As shown in FIG. 4A, the enhancement of beta-arrestin recruitment was increased (as demonstrated by the increase of blue/green fluorescent ratio) after IL-8 stimulation. The enhancement was inhibited by anti-CXCR2 mAb (NICR2-5) (100 μg/ml) but not control normal IgG1 (100 μg/ml). The present invention next investigated the intracellular level of cAMP by using Cisbio CAMP-Gi assay kit. Cells (3000 cells/well) were seeded onto the 96-well plates and cultured at 37° C. overnight. Cells were treated with different combinations of antibodies (100 μg/ml) and IL-8 (300 ng/ml) for 16 h. The intracellular cAMP level was determined by using Cisbio assay kit and the intensities at 620 and 650 nm were detected by SpectraMax iD5 Reader. Because CXCR2-coupled G protein is Gi (inhibitory G protein), treatment of IL-8 (300 ng/ml) decreased intracellular cAMP level and addition of anti-CXCR2 mAb, but not control IgG1, counteracted the decrease of cAMP (FIG. 4B).

Figure 5:
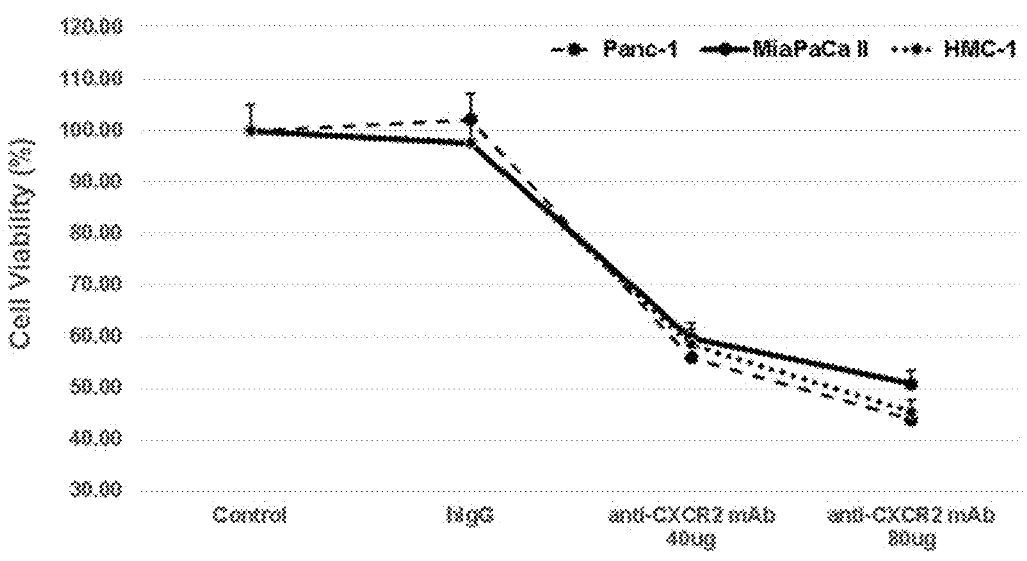
FIG. 5 shows the growth inhibition of pancreatic cancer cells and leukemia cells by humanized anti-CXCR2 mAb (NICR2-5) in cell culture. Pancreatic cancer cells and leukemia cells are seeded on 24 well-plates and incubated without or with control IgG (hlgG) and humanized anti-CXCR2 mAb (NICR2-5) of varying concentration (0 μg, 40 μg, 80 μg). The growth inhibition is quantified by MTS cell proliferation assay. The experiment is performed with 3 different cell lines with triplicates in 2 independent experiments.

Humanized Anti-CXCR2 mAb (NICR2-5) Inhibits the Proliferation of Cancer Cells In Vitro To test the anti-cancer effect of the humanized anti-CXCR2 mAb (NICR2-5), leukemia (HMC-1) and pancreatic (Panc-1 and MiaPaca-II) cancer cells (3000 cells/well) were seeded onto the 96-well plates and cultured at 37° C. overnight. Cells were treated with different combinations of control IgG1 or humanized anti-CXCR2 mAb (NICR2-5) for 48 h. Cell proliferation was assessed by adding 2,3,5-Triphenyl-tetrazolium chloride (MTS) developing reagent. The reaction was terminated 2 h after the addition of developing reagent. The intensities at 490 nm in each well was measured and were compared to the mock control wells. The humanized anti-CXCR2 mAb (NICR2-5) but not control IgG1 inhibited the proliferation of cancer cells in a dose-dependent manner (FIG. 5).

Figure 6:
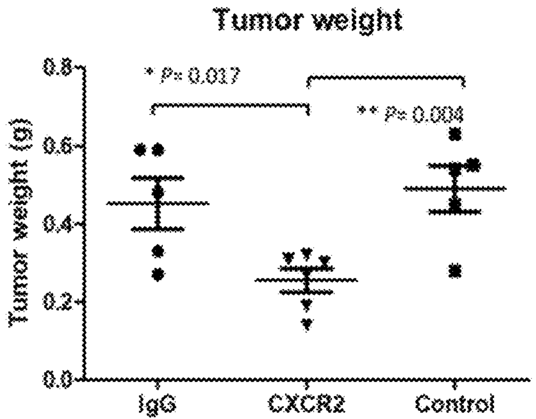
FIG. 6 shows that humanized anti-CXCR2 mAb (NICR2-5) inhibits tumor growth of the pancreatic cancer cells in an orthotopic model. The mice (n=5 for the treatment with IgG group, n=6 for the treatment with anti-CXCR2 monoclonal antibody group (CXCR2) and n=5 for control group) are sacrificed one week after the end of anti-CXCR2 monoclonal antibody treatment. The tumor weight and tumor volume of the control and anti-CXCR2 monoclonal antibody treatment groups are compared. Error bars are Means±SEM. * $p<0.05$.
Figure 6:
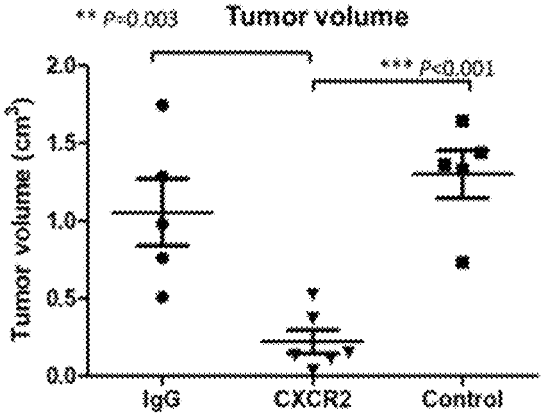

Humanized Anti-CXCR2 mAb (NICR2-5) Inhibits the Proliferation of Cancer Cells In Vivo To test the therapeutic effect in vivo, the luciferase-tagged Panc-1 pancreatic cancer cells ($1\times10^6$ cells) were injected into the pancreas of severe combined immunodeficient (SCID) mice. Two weeks later, normal IgG1 or humanized anti-CXCR2 mAb (NICR2-5) (30 mg/kg) was given by intravenous injection twice a week for consecutive two weeks. After four treatment, mice were hosted for another one week and were sacrificed. Tumor growth was monitored by the IVIS imaging system. The tumor weight and volume were measured (FIG. 6). The results demonstrated that humanized anti-CXCR2 mAb (NICR2-5) suppressed tumor growth of Panc-1 pancreatic cancer cells in the orthotopic model.

Figure 7A:
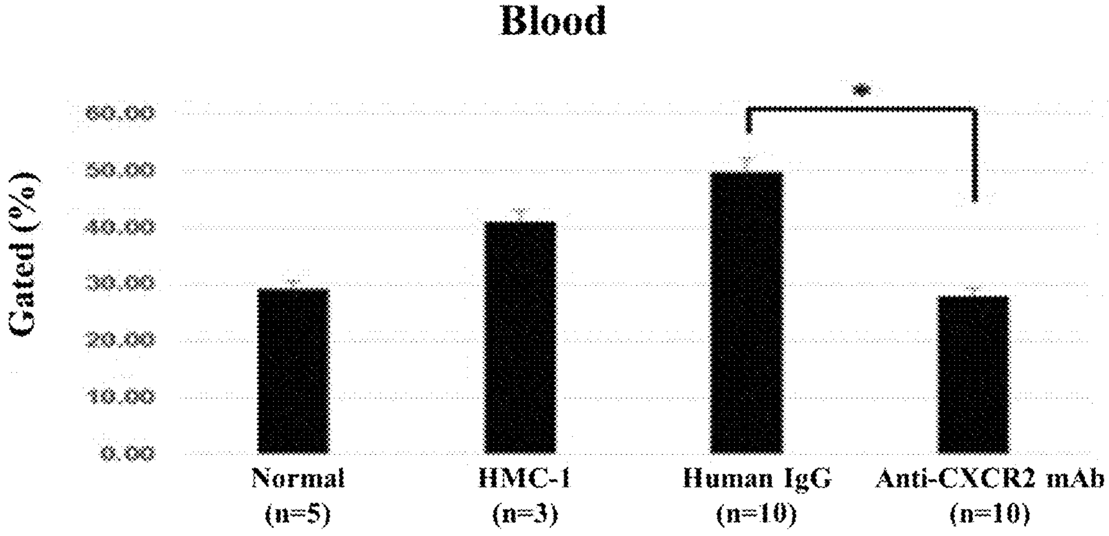
FIG. 7A shows the numbers of $hCD68^+$ cells in the blood of mice in different experimental groups.
Figure 7B:
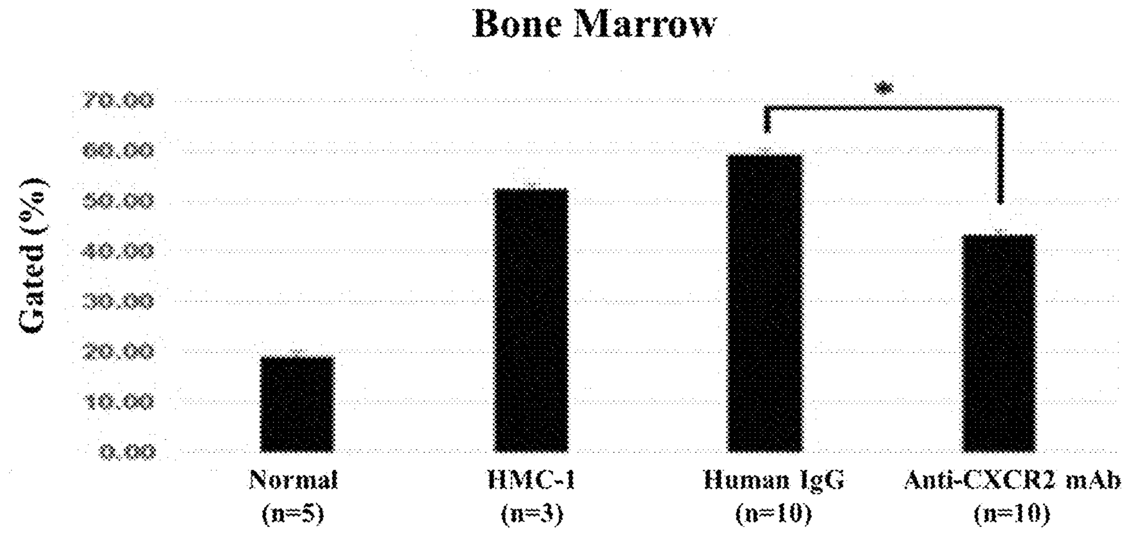
FIG. 7B shows the numbers of $hCD68^+$ cells in the bone marrow of mice in different experimental groups. * $P<0.05$. n: number.

In another in vivo model, HMC-1 leukemia cells were intravenously injected into SCID mice. One week later, normal IgG1 or humanized anti-CXCR2 mAb (NICR2-5) was given at a dose of 30 mg/kg twice per week. The mice were treated with antibody for 7 times and were sacrificed at day 27 after cancer cell injection. Blood and bone marrow of the mice were harvested and the percentage of human leukemia cells detected by $hCD68^+$ was investigated by flow cytometric analysis. As shown in FIG. 7A, the numbers of $hCD68^+$ cells in blood were significantly decreased in mice treated with anti-CXCR2 monoclonal antibody. In addition, the numbers of $hCD68^+$ cells in bone marrow were also reduced (FIG. 7B). These findings demonstrate the functionally active humanized anti-CXCR2 mAb (NICR2-5) of the present invention can inhibit pancreatic cancer and leukemia cells in animals.

Those skilled in the art recognize the foregoing outline as a description of the method for communicating hosted application information. The skilled artisan will recognize that these are illustrative only and that many equivalents are possible.

What is claimed is:

1. An isolated antibody that binds to chemokine C-X-C motif receptor 2 (CXCR2), comprising a light chain and a heavy chain, wherein the variable region of the light chain comprises a CDR-L1 having the sequence of SEQ ID NO: 3, a CDR-L2 having the sequence of SEQ ID NO: 4 and a CDR-L3 having the sequence of SEQ ID NO: 5, and the variable region of the heavy chain comprises a CDR-H1 having the sequence of SEQ ID NO: 6, a CDR-H2 having the sequence of SEQ ID NO: 7 and a CDR-H3 having the sequence of SEQ ID NO: 8.

2. The isolated antibody of claim 1, wherein the isolated antibody inhibits CXCR2 activity.

3. A method for treating a subject suffering from pancreatic cancer, comprising administering to the subject with pancreatic cancer a composition comprising the antibody of claim 1.

4. The method of claim 3, wherein the antibody inhibits cancer cell proliferation and tumor growth of the pancreatic cancer.

5. The method of claim 3, wherein a therapeutically effective amount of the antibody ranges from 1 to 100 mg/kg of body weight.

6. A method for treating a subject suffering from leukemia, comprising administering to the subject with leukemia a composition comprising the antibody of claim 1.

7. The method of claim 6, wherein the leukemia comprises acute lymphoblastic leukemia (ALL), acute myeloid leukemia (AML), chronic lymphocytic leukemia (CLL), chronic myeloid leukemia (CML), chronic myelomonocytic leukemia (CMML) or hairy cell leukemia (HCL).

8. The method of claim 6, wherein the antibody inhibits leukocyte proliferation of the leukemia.

9. The method of claim 8, wherein the leukocyte comprises mast cell.

10. The method of claim 6, wherein a therapeutically effective amount of the antibody ranges from 1 to 100 mg/kg of body weight.

* * * * *